(12) United States Patent
Yamashita et al.

(10) Patent No.: US 10,781,194 B2
(45) Date of Patent: Sep. 22, 2020

(54) PROCESS FOR PREPARING (E2)-CIS-6,7-EPOXY-2-NONENAL

(71) Applicant: Shin-Etsu Chemical Co., Ltd., Tokyo (JP)

(72) Inventors: Miyoshi Yamashita, Niigata (JP); Yuki Miyake, Niigata (JP); Takeshi Kinsho, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/545,887

(22) Filed: Aug. 20, 2019

(65) Prior Publication Data

US 2020/0062725 A1  Feb. 27, 2020

(30) Foreign Application Priority Data

Aug. 22, 2018  (JP) ................. 2018-155266

(51) Int. Cl.
*C07D 301/14*   (2006.01)
(52) U.S. Cl.
CPC ................. *C07D 301/14* (2013.01)
(58) Field of Classification Search
CPC ..... C07C 45/29; C07C 45/292; C07C 45/298; C07C 47/20; C07C 47/00; C07D 301/14
USPC ........................................................ 568/430
See application file for complete search history.

(56) References Cited

U.S. PATENT DOCUMENTS 3,444,216 A * 5/1969 Doering .................. C07C 45/29
552/572
2014/0275631 A1 9/2014 Abril-Horpel et al.

FOREIGN PATENT DOCUMENTS

WO  2011145048  11/2011

OTHER PUBLICATIONS

Frerot "Easy Access to Aroma Active Unsaturated γ-Lactones by Addition of Modified Titanium Homoenolate to Aldehydes" J. Agric. Food Chem. 2011, 59, 4057-4061.*
Extended European Search Report corresponding to European Patent Application No. 19193038.7 (7 pages) (dated Dec. 19, 2019).
Tojo et al. "Oxidation of alcohols to aldehydes and ketones, Chapter 2: Activated Dimethyl Sulfoxide" Oxidation of Alcohols to Aldehydse and Ketones: A Guide to Current Common Practice (Book Series: Basic Reactions in Organic Synthesis), pp. 97-179 (2006).
Extended European Search Report corresponding to European Patent Application No. 19193077.5 (8 pages) (dated Nov. 4, 2019).

Frerot et al. "Easy Access to Aroma Active Unsaturated gamma-Lactones by Addition of Modified Titanium to Homoenolate Aldehydes" Journal of Agricultural and Food Chemistry, 59:4057-4061 (2011).
Mori, Kenji "Pheromone synthesis. Part 263: Synthesis of the racemate and the enantiomers of (E)-cis-6,7-epoxy-2-nonenal, the male-produced pheromone of the red-necked longhorn beetle, *Aromia bungii*" Tetrahedron, 74:1444-1448 (2018).
Matikainen et al. "A study of 1,5-hydrogen shift and cyclization reactions of an alkali isomerized methyl linolenoate" Tetrahedron, 59:567-573 (2003).
Mustafa et al. "A nine carbon homologating system for skip-conjugated polyenes" Chemistry and Physics of Lipids, 183:34-42 (2014).
Reid et al. "Two carbon homologated alpha,beta-unsaturated aldehydes from alcohols using the in situ oxidation—Wittig reaction" Chemical Communications, 18:2284-2285 (2003).
Sondheimer, Franz "Synthesis of the Violet Leaf Perfume, 2(trans),6(cis)-Nonadienal" Journal of the American Chemical Society, 74(16):4040-4043 (1952).
Xu et al. "Identification of a male-produced sex-aggregation pheromone for a highly invasive cerambycid beetle, *Aromia bungii*" Scientific Reports, 7(7330):1-7 (2017).

\* cited by examiner

*Primary Examiner* — David K O'Dell
(74) *Attorney, Agent, or Firm* — Myers Bigel, P.A.

(57) ABSTRACT

The object of the present invention is to provide an industrial and economical process for preparing (E2)-cis-6,7-epoxy-2-nonenal of the following formula (3):

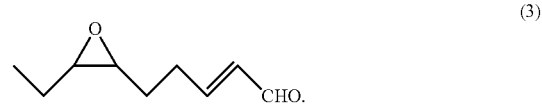

(3)

The present invention provides a process for preparing (E2)-cis-6,7-epoxy-2-nonenal (3), comprising at least steps of:
subjecting (Z3,Z6)-3,6-nonadien-1-ol of the following formula (1) to oxidation:

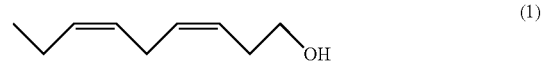

(1)

to form (E2,Z6)-2,6-nonadienal of the following formula (2); and

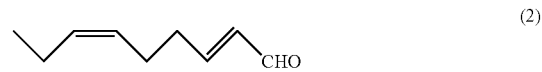
(2)

epoxidizing the resulting (E2,Z6)-2,6-nonadienal to form the aforesaid (E2)-cis-6,7-epoxy-2-nonenal (3).

3 Claims, No Drawings

PROCESS FOR PREPARING (E2)-CIS-6,7-EPOXY-2-NONENAL

CROSS-REFERENCE TO RELATED APPLICATION

This U.S. nonprovisional application claims priority to Japanese Application No. 2018-155266 filed Aug. 22, 2018, the entire contents of which are incorporated herein by reference.

TECHNICAL FIELD

The present invention relates to a process for preparing (E2)-cis-6,7-epoxy-2-nonenal which is known as an aggregation pheromone of red-necked longhorn beetle (scientific name: *Aromia bungii*).

BACKGROUND ART

Larvae of the red-necked longhorn beetle eat or bore trunks of Rosaceae trees such as cherry, Japanese apricot, peach, and plum to thereby damage these trees. Weakening or blighting of these trees due to the damage has become a serious problem. Invasion of them into Japan was found for the first time in 2012 and they were designated as a "Quarantine Pest".

For control of the red-necked longhorn beetle, trapping of adult insects, sticking of larvae present inside trunks with needles, and injection of an insecticide into their invasion hole have been carried out, but these methods are not sufficiently effective. There is therefore a demand for the development of a new highly-effective control method.

Mating disturbance or mass trapping using a pheromone of the insects is expected as one of the new control methods. Tian Xu et al. report that the aggregation pheromone of the red-necked longhorn beetle is (E2)-cis-6,7-epoxy-2-nonenal (Non-Patent Literature 1 mentioned below).

Xu et. al. report a process for preparing (E2)-cis-6,7-epoxy-2-nonenal by epoxidizing the olefinic moiety at position 6 of (E2,Z6)-2,6-nonadienal with m-chloroperbenzoic acid (Non-Patent Literature 1).

LIST OF THE PRIOR ART

[Non-Patent Literature 1] Tian Xu et. al., Scientific Reports, 7, 7330 (2017)

SUMMARY OF THE INVENTION

However, the process for preparing (E2)-cis-6,7-epoxy-2-nonenal reported in Non-Patent Literature 1 has a problem that it is difficult and costly to obtain the starting material, (E2,Z6)-2,6-nonadienal in a large scale.

The present invention has been made in these circumstances, and aims to overcome the aforesaid problem of the prior art and provide an industrial and economical process for preparing (E2)-cis-6,7-epoxy-2-nonenal.

As a result of intensive researches, the present inventors have found that (E2,Z6)-2,6-nonadienal can be prepared industrially and economically by subjecting, to oxidation, (Z3,Z6)-3,6-nonadien-1-ol which is known as a flavoring agent and can be obtained industrially in a large amount, and that (E2)-cis-6,7-epoxy-2-nonenal can be industrially prepared from (E2,Z6)-2,6-nonadienal at low costs, and thus have completed the present invention.

According to one aspect of the present invention, there is provided a process for preparing (E2)-cis-6,7-epoxy-2-nonenal of the following formula (3):

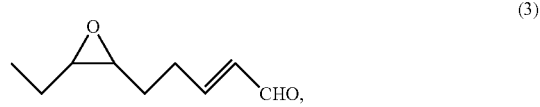

(3)

the process comprising at least steps of:
subjecting (Z3,Z6)-3,6-nonadien-1-ol of the following formula (1) to oxidation:

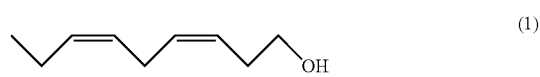

(1)

to form (E2,Z6)-2,6-nonadienal of the following formula (2): and

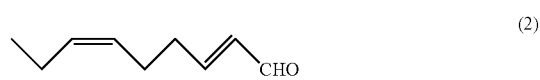

(2)

epoxidizing the resulting (E2,Z6)-2,6-nonadienal to form the aforesaid (E2)-cis-6,7-epoxy-2-nonenal (3).

An embodiment of the present invention makes it possible to efficiently, industrially, and economically prepare (E2)-cis-6,7-epoxy-2-nonenal which is known as an aggregation pheromone of red-necked longhorn beetle.

DETAILED DESCRIPTION OF THE PREFERRED EMBODIMENTS

The process for preparing (E2)-cis-6,7-epoxy-2-nonenal according to the present invention will hereinafter be described.

A. Oxidation Step

The oxidation step comprises a step of subjecting (Z3,Z6)-3,6-nonadien-1-ol of the following formula (1) to oxidation to form (E2,Z6)-2,6-nonadienal of the following formula (2).

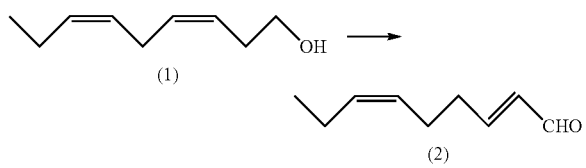

1. (Z3,Z6)-3,6-Nonadien-1-ol (1) as a Starting Material (Z3,Z6)-3,6-nonadien-1-ol (1) is commercially available or may be synthesized in house.

2. Oxidation

The oxidation may be carried out, for example, by reacting (Z3,Z6)-3,6-nonadien-1-ol (1) with an oxidizing agent in a solvent.

Examples of the oxidizing agent include (a) a hypervalent iodine compound, (b) a chromic acid compound, (c) a sulfoxide compound, (d) a manganese compound, (e) a nitroxyl radical compound, and (f) a perruthenate compound. In view of the yield or the selectivity for regioisomers, (a) a hypervalent iodine compound, (b) a chromic acid compound, and (c) a sulfoxide compound are preferred, and (c) a sulfoxide compound is more preferred. The oxidizing agent may be used either alone or in combination thereof if necessary. The oxidizing agent may be commercially available one.

(a) Hypervalent Iodine Compound

Examples of the hypervalent iodine compound include 2-iodoxybenzoic acid, 1,1,1-triacetoxy-1,1-dihydro-1,2-benziodoxol-3(1H)-one, and 2-iodoxy-5-methylbenzenesulfonic acid. The 2-iodoxy-5-methylbenzenesulfonic acid can be prepared, for example, by reacting potassium 2-iodo-5-methylbenzenesulfonate with a monopersulfate such as a potassium monopersulfate.

(b) Chromic Acid Compound

Examples of the chromic acid compound include a chromium trioxide pyridine complex, pyridinium chlorochromate, and pyridinium dichromate.

(c) Sulfoxide Compound

The sulfoxide compound is represented by the following formula (4):

$$CH_3(R^1)S=O \quad (4)$$

(hereinafter referred to as "sulfoxide compound (4)").

$R^1$ in the formula (4) represents a monovalent hydrocarbon group having from 1 to 12, preferably from 1 to 6, carbon atoms.

Examples of $R^1$ include linear saturated hydrocarbon groups such as methyl, ethyl, 1-propyl, 1-butyl, 1-pentyl, 1-hexyl, 1-heptyl, l-octyl, 1-nonyl, 1-decyl, l-undecyl, and 1-dodecyl groups; branched saturated hydrocarbon groups such as 1,1-dimethylethyl, 1-methylethyl, 2-methylpropyl, and 2-methylbutyl groups; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; aryl groups such as a phenyl group; and aralkyl groups such as a benzyl group. Isomers thereof are also included. The hydrogen atoms of the hydrocarbon groups may be substituted with a group such as a methyl or ethyl group.

$R^1$ is preferably a methyl, ethyl, 1-propyl, or l-dodecyl group in view of the reactivity or the handling.

Examples of the sulfoxide compound (4) include dimethyl sulfoxide, methyl ethyl sulfoxide, methyl propyl sulfoxide, methyl butyl sulfoxide, methyl pentyl sulfoxide, methyl dodecyl sulfoxide, methyl 1-methylethyl sulfoxide, methyl 2-methylpropyl sulfoxide, methyl 1,1-dimethylethyl sulfoxide, methyl phenyl sulfoxide, and methyl benzyl sulfoxide. The sulfoxide compound (4) is preferably dimethyl sulfoxide, and methyl dodecyl sulfoxide in view of the price, the availability, the reactivity, or the odor of byproducts. The sulfoxide compound (4) may be used either alone or in combination thereof if necessary.

(d) Manganese Compound

Examples of the manganese compound include manganese dioxide and barium manganate.

(e) Nitroxyl Radical Compound

Examples of the nitroxyl radical compound include 2,2,6,6-tetramethylpiperidine 1-oxyl, 4-hydroxy-2,2,6,6-tetramethylpiperidine 1-oxyl, 2-azaadamantane N-oxyl, 1-methyl-2-azaadamantane N-oxyl, and 9-azanoradamantane N-oxyl.

(f) Perruthenate Compound

Examples of the perruthenate compound include ammonium perruthenate compounds such as tetrapropylammonium perruthenate.

The oxidizing agent such as (a) to (f) above is added preferably in an amount of from 1.0 mol to 70.0 mol, more preferably from 1.5 mol to 50.0 mol, per mol of (Z3,Z6)-3,6-nonadien-1-ol (1) in view of the reactivity or the yield.

When the sulfoxide compound (c) is used as the oxidizing agent, an activator is preferably used together.

Examples of the activator include sulfur trioxide complexes, acid anhydrides, carbodiimide compounds, oxalyl chloride, and phosphorus pentaoxide. The activator may be commercially available one.

Examples of the sulfur trioxide complexes include a sulfur trioxide pyridine complex, a sulfur trioxide trimethylamine complex, a sulfur trioxide triethylamine complex, a sulfur trioxide ethyldiisopropylamine complex, and a sulfur trioxide N,N-dimethylformamide complex. The sulfur trioxide complex is preferably a sulfur trioxide pyridine complex in view of the reactivity. The sulfur trioxide complex may be used either alone or in combination thereof if necessary.

Examples of the acid anhydrides include acetic anhydride and trifluoroacetic anhydride.

Examples of the carbodiimide compounds include dicyclohexylcarbodiimide, diisopropylcarbodiimide, and 1-ethyl-3-(3-dimethylaminopropyl)carbodiimide hydrochloride.

The activator is used preferably in an amount of from 1.0 mol to 10.0 mol, more preferably from 2.0 mol to 5.0 mol, still more preferably from 2.5 mol to 3.5 mol, per mol of (Z3,Z6)-3,6-nonadien-1-ol (1) in view of the reactivity or the yield.

A molar ratio of the oxidizing agent (sulfoxide compound) to the activator is preferably from 10.0 to 15.0 in view of the reactivity or the yield.

The activator may be added after diluted with a proper solvent, for example, dimethylsulfoxide, methylene chloride, chloroform, ethyl acetate, or toluene.

When the sulfur trioxide complex, acid anhydride, carbodiimide compound, oxalyl chloride or phosphorus pentaoxide is used as the activator, a base is preferably used as an auxiliary agent for the aforesaid oxidation.

Examples of the base include an amine compound of the following formula (5):

$$N(R^2)(R^3)(R^4) \quad (5)$$

(hereinafter referred to as "the amine compound (5)") and a heterocyclic aromatic amine compound.

$R^2$, $R^3$, and $R^4$ in the formula (5) each independently represent a monovalent hydrocarbon group having from 1 to 12, preferably from 1 to 6, carbon atoms, or $R^3$ and $R^4$ may be bonded to each other to form a divalent hydrocarbon group having from 3 to 12, preferably from 3 to 6, carbon atoms, $R^3$-$R^4$.

$R^2$, $R^3$, and $R^4$ may be the same with as or different from $R^1$ defined for the sulfoxide compound (4).

Examples of the divalent hydrocarbon group, $R^3$-$R^4$, include linear saturated hydrocarbon groups such as 1,3-propylene, 1,4-butylene, 1, 5-pentylene, 1, 6-hexylene, 1, 7-heptylene, 1, 8-octylene, 1, 9-nonylene, 1, 10-decylene, 1, 11-undecylene, and 1,12-dodecylene groups; branched saturated hydrocarbon groups such as 2,2-dimethyl-1,3-propylene, 1,3-butylene, and 2,3-dimethyl-1,3-butylene groups; linear unsaturated hydrocarbon groups such as 1,3-propenylene and 1,4-butenylene groups; branched unsaturated hydrocarbon groups such as 2-methylidene-1,3-propylene group; and cyclic hydrocarbon groups such as 1,2-cyclopropylene and 1,2-cyclobutylene groups. Isomers thereof are also included. The hydrogen atoms of the hydrocarbon groups may be substituted with a group such as a methyl or ethyl group.

Examples of the amine compound (5) include trialkylamine compound such as trimethylamine, triethylamine, tripropylamine, tributylamine, trioctylamine, tridodecylamine, diisopropylethylamine, dimethyloctylamine, and didodecylethylamine; and cyclic tertiary amine compound such as N-methylpiperidine, N-ethylpiperidine, N-butylpiperidine, N-methylpyrrolidine, N-ethylpyrrolidine, and N-butylpyrrolidine. The amine compound (5) is preferably trimethylamine, triethylamine, and tripropylamine in view of the price, the availability, or the reactivity. The amine compound (5) may be used either alone or in combination thereof if necessary. The amine compound (5) may be commercially available one.

Examples of the heterocyclic aromatic amine compound include pyridine and quinoline. The heterocyclic aromatic amine compound may be used either alone or in combination thereof if necessary. The heterocyclic aromatic amine compound may be commercially available one.

The base is used preferably in an amount of from 1.0 mol to 10.0 mol, more preferably from 3.0 mol to 6.0 mol, per mol of (Z3,Z6)-3,6-nonadien-1-ol (1) in view of the reactivity or the yield.

A molar ratio of the base to the activator is preferably from 1.0 to 2.0, more preferably from 1.5 to 1.8, in view of the reactivity or the yield.

When the carbodiimide compound is used as the activator, an acid may be used together.

Examples of the acid include trifluoroacetic acid, difluoroacetic acid, trichloroacetic acid, dichloroacetic acid, monochloroacetic acid, cyanoacetic acid, orthophosphoric anhydride, and phosphorous acid. The acid is preferably trifluoroacetic acid, dichloroacetic acid, or orthophosphoric anhydride in view of the reactivity. These acids may be used either alone or in combination thereof if necessary. The acid may be commercially available one.

The amount of the acid is preferably from 0.3 mol to 2.0 mol, more preferably from 0.3 mol to 0.5 mol, per mol of (Z3,Z6)-3,6-nonadien-1-ol (1) in view of the reactivity or the by-production amount of an impurity.

When the nitroxyl radical compound (e) is used as the oxidizing agent, a hypochlorite or iodobenzene diacetate may be used as a re-oxidizing agent if necessary.

When the perruthenate compound (f) is used as the oxidizing agent, an amine oxide compound such as N-methylmorpholine oxide may be used as a re-oxidizing agent if necessary.

A solvent may be used in the oxidation, if necessary.

The solvent used in the oxidation is not particularly limited insofar as it does not adversely affect the oxidation. Examples of the solvent include a halogen-based solvent such as methylene chloride, chloroform, carbon tetrachloride, trichloroethane, and tetrachloroethane and a hydrocarbon-based solvent such as pentane, hexane, heptane, and cyclohexane. The solvent is preferably methylene chloride in view of the reactivity or the yield. The solvent used in the oxidation may be used either alone or in combination thereof if necessary. The solvent may be commercially available one.

The sulfoxide compound (4) or the base used in the oxidation may serve also as a solvent.

The solvent is used preferably in an amount of from 1000.0 g to 10000.0 g, more preferably from 3000.0 g to 8000.0 g, per mol of (Z3,Z6)-3,6-nonadien-1-ol (1) in view of the economy or the reactivity.

A reaction temperature is preferably from −50° C. to 80° C., more preferably from 0° C. to 50° C., in view of the reaction rate or the yield.

The duration of the oxidation may vary, depending on, for example, a solvent and a production scale. It ranges preferably from 1 hour to 30 hours, more preferably from 1 hour to 12 hours, in view of the productivity.

The present inventors have found that when the oxidation is carried out particularly preferably with sulfoxide compound (4) in the presence of the sulfur trioxide complex, and the amine compound (5), the hydroxyl group of the (Z3, Z6)-3,6-nonadien-1-ol (1) may be oxidized into an aldehyde group, and at the same time, rearrangement of the double bond at position 3 to position 2 and then isomerization is proceed sufficiently.

Examples of a combination of the sulfoxide compound (4) with the sulfur trioxide complex and the amine compound (5) include a combination of dimethyl sulfoxide, a sulfur trioxide pyridine complex and triethylamine, a combination of methyl dodecyl sulfoxide, a sulfur trioxide pyridine complex, and triethylamine, and a combination of dimethyl sulfoxide, a sulfur trioxide pyridine complex, and tripropylamine.

In the aforesaid conditions for oxidation, i.e., with the sulfoxide compound (4) in the presence of the sulfur trioxide complex and the amine compound (5), (E2,Z6)-2,6-nonadienal (2) can be produced in a high purity, a high yield, and a high selectivity.

In an embodiment of the present invention, the oxidation may be carried out with a sulfoxide compound of the following formula (4):

in which $R^1$ represents a monovalent hydrocarbon group having from 1 to 12 carbon atoms, in the presence of a sulfur trioxide complex and an amine compound of the following formula (5):

in which $R^2$, $R^3$, and $R^4$ each independently represent a monovalent hydrocarbon group having from 1 to 12 carbon atoms, or $R^3$ and $R^4$ may be bonded to each other to form a divalent hydrocarbon group having from 3 to 12 carbon atoms, $R^3$-$R^4$.

B. Epoxidation Step

The epoxidation step comprises a step of epoxidizing (E2,Z6)-2,6-nonadienal (2) to form (E2)-cis-6,7-epoxy-2-nonenal of the following formula (3).

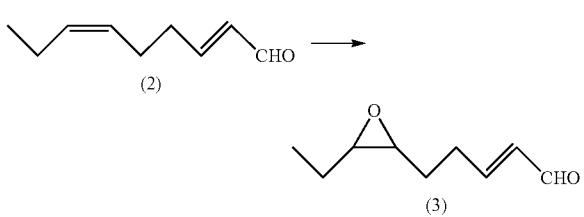

The epoxidation may be carried out, for example, by reacting the (E2,Z6)-2,6-nonadienal (2) with an epoxidizing agent in a solvent.

Examples of the epoxidizing agent include an organic percarboxylic acid compound having from 1 to 7 carbon atoms such as performic acid, peracetic acid, perpropionic acid, pertrifluoroacetic acid, perbenzoic acid, m-chloroperbenzoic acid, and 4-nitroperbenzoic acid and dioxirane compound such as 3,3-dimethyl-1,2-dioxirane, 3-ethyl-3-methyl-1,2-dioxirane, 3-methyl-3-trifluoromethyl-1,2-dioxirane, 3,3-difluoro-1,2-dioxirane, and 1,2-dioxaspiro[2,5]octane. The epoxidizing agent is preferably performic acid, peracetic acid or m-chloroperbenzoic acid, more preferably m-chloroperbenzoic acid, in view of the reactivity, the yield or the handling ease. The epoxidizing agent may be used either alone or in combination thereof if necessary. The epoxidizing agent may be commercially available one.

The epoxidizing agent is used preferably in an amount of from 1.0 mol to 3.0 mol, more preferably from 1.0 mol to 1.5 mol, per mol of (E2,Z6)-2,6-nonadienal (2) in view of the economy or the reactivity.

The epoxidation may be asymmetric epoxidation in the Jacobsen-Katsuki epoxidation conditions or the Shi asymmetric epoxidation conditions.

When the organic percarboxylic acid compound is used as the epoxidizing agent, an alkali metal hydrogencarbonate such as sodium hydrogencarbonate may be added to the reaction system, if necessary, to prevent the reaction system from becoming acidic due to a carboxylic acid compound derived from the organic percarboxylic acid compound.

Examples of the solvent to be used in the epoxidation include halogen-based solvents such as methylene chloride, chloroform, carbon tetrachloride, trichloroethane, and tetrachloroethane; hydrocarbon solvents such as pentane, hexane, heptane, and cyclohexane; aromatic solvents such as benzene and toluene; ether solvents such as diethyl ether, tetrahydrofuran, 1,4-dioxane, t-butyl methyl ether, and methyltetrahydropyran; ester solvents such as methyl acetate, ethyl acetate, and butyl acetate; and nitrile solvents such as acetonitrile. The solvent to be used in the epoxidation is preferably dichloromethane, chloroform, tetrahydrofuran, or ethyl acetate in view of the reactivity or the yield. These solvents may be used either alone or in combination thereof if necessary. The solvent may be commercially available one.

The solvent is used preferably in an amount of from 1000.0 g to 5000.0 g, more preferably from 2000.0 g to 4000.0 g, per mol of (E2,Z6)-2,6-nonadienal (2) in view of the economy or the reactivity.

A reaction temperature is preferably from −30° C. to 50° C., more preferably from −10° C. to 30° C., in view of the reaction rate or the yield.

The duration of the epoxidation may vary, depending on, for example, a solvent and a production scale. It ranges preferably from 1 hour to 30 hours, more preferably from 1 hour to 15 hours, in view of the productivity.

C. Final Product (E2)-cis-6,7-epoxy-2-nonenal (3)

Examples of (E2)-cis-6,7-epoxy-2-nonenal (3) include (E2,R6,S7)-6,7-epoxy-2-nonenal of the following formula (3-1):

(3-1)

and (E2,S6,R7)-6,7-epoxy-2-nonenal of the following formula (3-2):

(3-2)

and a mixture thereof.

EXAMPLES

The present invention will be further described with reference to the following Examples. It should be construed that the present invention is not limited to or by the Examples.

The term "purity" as used herein means an area percentage obtained by gas chromatography (GC) analysis unless otherwise specified. The term "production ratio" means a relative ratio of area percentages obtained by GC analysis. The term "yield" means a weight percentage of a product calculated from the area percentages obtained by GC analysis. This yield is thus a reduced yield based on the GC area percentages. Since a raw material and a product in the reaction do not always have a purity of 100%, a yield is reduced by the following equation: reduced yield (%)= ([(weight of a product obtained by reaction×a GC area percent)/molecular weight of a product]÷[(weight of a starting material×a GC area percent)/molecular weight of a starting material])×100. The detection sensitivities in GC may differ among the compounds, so that a reduced yield may sometimes exceed 100%, particularly when the raw material and/or the product are crude.

GC conditions: GC: Capillary gas chromatograph GC-2010, ex Shimadzu Corporation; column: DB-5, 0.25 mm×0.25 mmϕ×30 m; carrier gas: He (1.55 mL/min); detector: FID; column temperature: held at 60° C. for 3 minutes and then elevated to 250° C. at a rate of 10° C./min.

Example 1

Preparation of (E2,Z6)-2,6-nonadienal (2)

Air in a reactor equipped with a stirrer, a condenser, and a thermometer was purged with nitrogen. Then, to the reactor were added (Z3,Z6)-3,6-nonadien-1-ol (1) (140.22 g, 1.0 mol), triethylamine (505.95 g, 5.0 mol), and methylene chloride (5000.0 g) and the temperature was maintained at from 20 to 25° C. A solution of a sulfur trioxide pyridine complex (477.48 g, 3.0 mol) in dimethylsulfoxide (2968.9 g, 38.0 mol) was added dropwise to the resulting reaction mixture at from 25° C. to 28° C. over 2 hours and stirred for 5 hours. Then, the mixture was cooled to 0° C. and an aqueous 5.0 wt % hydrochloric acid (3000.0 g) was added while preventing the temperature of the mixture from exceeding 25° C. Then, the resulting mixture was separated into layers and the aqueous layer was removed. The organic layer thus obtained was washed successively with water (2400.0 g), an aqueous 5.0 wt % sodium hydrogencarbonate solution (2500.0 g) and an aqueous 10.0 wt % sodium chloride solution (2400.0 g). The solvent in the organic layer thus obtained was removed under a reduced pressure. The resulting concentrate was subjected to distillation for purification to obtain (E2,Z6)-2,6-nonadienal (2) (boiling point: from 70 to 73° C./8 mmHg, 94.40 g: 0.68 mol, yield: 68.3%, purity: 86.9%). A production ratio, [(E2,Z6)-2,6-nonadienal (2)]: [(Z3,Z6)-3,6-nonadienal (1)], was 98.4:1.6.

The following are spectrum data of the (E2,Z6)-2,6-nonadienal (2) thus produced.

Nuclear magnetic resonance spectrum: $^1$H-NMR (500 MHz, CDCl$_3$): δ 0.95 (3H, t, J=7.45 Hz), 2.02 (2H, dq, J=7.6, 7.5 Hz), 2.24 (2H, dt, J=7.3, 7.3 Hz), 2.38 (2H, dt, J=7.1, 7.01 Hz), 5.29 (1H, dtt, J=10.8, 7.2, 1.7 Hz), 5.43 (1H, dtt, J=10.7, 6.5, 1.6 Hz), 6.11 (2H, dt, J=15.7, 8.0, 1.4 Hz), 6.82 (1H, dt, J=14.2, 7.8 Hz), 9.48 (1H, d, 8.0 Hz).

Nuclear magnetic resonance spectrum: $^{13}$C-NMR (126 MHz, CDCl$_3$): δ 14.05, 20.52, 25.37, 32.67, 43.71, 133.16, 133.25, 157.99, 193.95.

Mass spectrum EI-Mass spectrum (70 eV): m/z 138 (M$^+$), 123, 109, 94, 81, 70, 70, 69, 53, 41, 27.

Infrared absorption spectrum (ATR method): ν (cm$^{-1}$) 719, 973, 1105, 1133, 1175, 1303, 1455, 1637, 1693, 2734, 2874, 2933, 2963, 3008.

Example 2

Preparation of (E2)-cis-6,7-epoxy-2-nonenal (3)

Air in a reactor equipped with a stirrer, a condenser, and a thermometer was purged with nitrogen. Then, to the reactor were added (E2,Z6)-2,6-nonadienal (2) (138.21 g, 1.0 mol) obtained in Example 1 and methylene chloride (3000.0 g), and the resulting mixture was cooled to −5° C. To the resulting mixture was added an aqueous 30 wt % hydrous metachloroperbenzoic acid (308.2 g, 1.25 mol) at from −5° C. to 0*C over 3 hours, followed by stirring at from 0° C. to 5° C. for 10 hours. Next, precipitated crystals were filtered off and the filtrate was washed successively with an aqueous 10.0 wt % sodium thiosulfate solution (2000.0 g), an aqueous 2.0 wt % sodium hydroxide solution (2000.0 g), and an aqueous 20.0 wt % sodium chloride solution (2000.0 g). The solvent in the organic layer thus obtained was removed under a reduced pressure. The resulting concentrate was subjected to distillation for purification to obtain (E2)-6,7-epoxy-2-nonenal (3) (boiling point: from 70 to 72° C./1.5 mmHg, 127.9 g: 0.83 mol, yield: 82.6%, purity: 95.2%).

The following are the spectrum data of the (E2)-cis-6,7-epoxy-2-nonenal (3) thus produced.

Nuclear magnetic resonance spectrum $^1$H-NMR (500 MHz, CDCl$_3$): δ 1.02 (3H, t, J=7.5 Hz), 1.51 (2H, m), 1.65 (1H, m), 1.76 (1H, m), 2.51 (2H, m), 2.88 (1H, dt, J=6.5, 4.2 Hz), 2.92 (1H, dt, J=7.7, 3.8 Hz), 6.13 (1H, ddt, J=15.7, 7.6, 1.5 Hz), 6.87 (1H, dt, J=15.5, 6.7 Hz), 9.49 (1H, d, J=7.6 Hz).

Nuclear magnetic resonance spectrum $^{13}$C-NMR (126 MHz, CDCl$_3$): δ 10.46, 21.02, 26.16, 29.79, 56.16, 58.26, 133.28, 156.82, 193.69.

Mass spectrum EI-Mass spectrum (70 eV): m/z 125 (M$^+$-C$_2$H$_5$), 112, 97, 85, 68, 67, 59, 55, 41, 39, 29.

Infrared absorption spectrum (ATR method): ν (cm$^{-1}$) 816, 905, 975, 1016, 1095, 1129, 1311, 1391, 1458, 1638, 1691, 1731, 2877, 2936, 2971.

The invention claimed is:

1. A process for preparing (E2)-cis-6,7-epoxy-2-nonenal of the following formula (3):

the process comprising at least steps of:
subjecting (Z3,Z6)-3,6-nonadien-1-ol of the following formula (1) to oxidation:

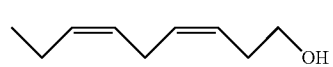

to form (E2,Z6)-2,6-nonadienal of the following formula (2);

wherein the oxidation is carried out with a sulfoxide compound of the following formula (4):

$$CH_3(R^1)S=O \qquad (4)$$

in which $R^1$ represents a monovalent hydrocarbon group having from 1 to 12 carbon atoms, in the presence of a sulfur trioxide complex and an amine compound of the following formula (5):

$$N(R^2)(R^3)(R^4) \qquad (5)$$

in which $R^2$, $R^3$, and $R^4$ each independently represent a monovalent hydrocarbon group having from 1 to 12 carbon atoms, or $R^3$ and $R^4$ may be bonded to each other to form a divalent hydrocarbon group having from 3 to 12 carbon atoms, $R^3$-$R^4$; and epoxidizing the resulting (E2,Z6)-2,6-nonadienal (2) to form the aforesaid (E2)-cis-6,7-epoxy-2-nonenal (3).

2. The process according to claim 1, wherein the sulfur trioxide complex is selected from the group consisting of a sulfur trioxide pyridine complex, a sulfur trioxide trimethylamine complex, a sulfur trioxide triethylamine complex, a sulfur trioxide ethyldiisopropylamine complex, and a sulfur trioxide N,N-dimethylformamide complex.

3. The process according to claim 1, wherein the amine compound is selected from the group consisting of a trialkylamine compound and a cyclic tertiary amine compound.

* * * * *

UNITED STATES PATENT AND TRADEMARK OFFICE
CERTIFICATE OF CORRECTION

| | |
|---|---|
| PATENT NO. | : 10,781,194 B2 |
| APPLICATION NO. | : 16/545887 |
| DATED | : September 22, 2020 |
| INVENTOR(S) | : Yamashita et al. |

It is certified that error appears in the above-identified patent and that said Letters Patent is hereby corrected as shown below:

In the Specification

Column 8, Line 19: Please correct "+" to read -- ÷ --

Signed and Sealed this
Eleventh Day of July, 2023

*Katherine Kelly Vidal*
Katherine Kelly Vidal
*Director of the United States Patent and Trademark Office*